(12) United States Patent
Nishio et al.

(10) Patent No.: US 9,193,938 B2
(45) Date of Patent: Nov. 24, 2015

(54) DETERGENT COMPOSITIONS FOR ENDOSCOPE WASHERS

(71) Applicant: KAO CORPORATION, Tokyo (JP)

(72) Inventors: Masaya Nishio, Wakayama (JP); Tatsuya Sakai, Wakayama (JP)

(73) Assignee: KAO CORPORATION, Tokyo (JP)

( * ) Notice: Subject to any disclaimer, the term of this patent is extended or adjusted under 35 U.S.C. 154(b) by 0 days.

(21) Appl. No.: 14/361,210

(22) PCT Filed: May 28, 2013

(86) PCT No.: PCT/JP2013/064790
§ 371 (c)(1),
(2) Date: May 28, 2014

(87) PCT Pub. No.: WO2013/180135
PCT Pub. Date: Dec. 5, 2013

(65) Prior Publication Data
US 2014/0311529 A1    Oct. 23, 2014

(30) Foreign Application Priority Data
May 28, 2012   (JP) .................. 2012-121399

(51) Int. Cl.
| | | |
|---|---|---|
| C11D 1/722 | (2006.01) | |
| C11D 1/83 | (2006.01) | |
| C11D 3/00 | (2006.01) | |
| C11D 11/00 | (2006.01) | |
| A61B 19/00 | (2006.01) | |
| C11D 3/20 | (2006.01) | |
| C11D 10/04 | (2006.01) | |
| C11D 1/04 | (2006.01) | |

(52) U.S. Cl.
CPC .............. *C11D 1/722* (2013.01); *A61B 19/34* (2013.01); *C11D 1/83* (2013.01); *C11D 3/0026* (2013.01); *C11D 3/2075* (2013.01); *C11D 10/045* (2013.01); *C11D 11/0029* (2013.01); *C11D 11/0041* (2013.01); *A61B 2019/343* (2013.01); *C11D 1/04* (2013.01)

(58) Field of Classification Search
CPC ......... C11D 1/722; C11D 1/772; A61B 19/34
USPC .................. 134/22.14, 161; 510/161
See application file for complete search history.

(56) References Cited

U.S. PATENT DOCUMENTS

| 3,036,130 | A | * | 5/1962 | Jackson et al. ............... 544/177 |
| 5,532,405 | A | * | 7/1996 | Lyford, IV ...................... 560/99 |
| 5,767,056 | A | * | 6/1998 | Lenoir ............................ 510/423 |
| 6,083,875 | A | * | 7/2000 | Sato et al. ....................... 504/127 |
| 2003/0083314 | A1 | * | 5/2003 | Yiv et al. ......................... 514/78 |
| 2006/0113506 | A1 | * | 6/2006 | Man et al. ................... 252/186.1 |
| 2009/0197786 | A1 | * | 8/2009 | Perry et al. .................... 510/191 |
| 2010/0311633 | A1 | * | 12/2010 | Johnson et al. ............... 510/221 |
| 2012/0316097 | A1 | | 12/2012 | Maeyama et al. |
| 2013/0172228 | A1 | | 7/2013 | Bartelme et al. |
| 2014/0311529 | A1 | * | 10/2014 | Nishio et al. ............... 134/22.14 |

FOREIGN PATENT DOCUMENTS

| JP | 6-33100 A | | 2/1994 |
| JP | 6-80997 A | | 3/1994 |
| JP | 2000-96097 A | | 4/2000 |
| JP | 2006-219552 A | | 8/2006 |
| JP | 2006219552 A | * | 8/2006 |
| JP | 2006-335896 A | | 12/2006 |
| JP | 2006335896 A | * | 12/2006 |
| JP | 2009-144070 A | | 7/2009 |
| JP | 2010-519351 A | | 6/2010 |
| JP | 2010-163599 A | | 7/2010 |
| JP | 2010-235801 A | | 10/2010 |
| JP | 2011-12219 A | | 1/2011 |
| JP | 2012-140486 A | | 7/2012 |
| JP | 2012-140487 A | | 7/2012 |
| WO | WO 2011-105449 A1 | | 9/2011 |

OTHER PUBLICATIONS

Hashimoto, JP 2006-219552. Non-Machine English Translation.*
International Search Report for PCT/JP2013/064790 mailed on Sep. 3, 2013.

* cited by examiner

*Primary Examiner* — Nicole M Buie-Hatcher
*Assistant Examiner* — M. Reza Asdjodi
(74) *Attorney, Agent, or Firm* — Birch, Stewart, Kolasch & Birch, LLP

(57) ABSTRACT

The present invention relates to [1] a detergent composition for endoscope washers, including a nonionic surfactant (A) represented by the following formula (1), a branched-chain fatty acid having not less than 6 and not more than 10 carbon atoms or a salt thereof (B), a defoaming agent (C) and water, $$R-O-[(EO)_m/(PO)_n]-H \qquad (1)$$

wherein R represents a branched-chain alkyl group having not less than 7 and not more than 9 carbon atoms; EO represents an ethanediyloxy group; PO represents a propanediyloxy group; m and n each represent an average molar number of addition of the ethanediyloxy or propanediyloxy group in which m is a number of not less than 1 and not more than 30, and n is a number of not less than 2 and not more than 50; and the mark "/" represents that EO and PO may be added either in a random form or in a block form, and an order of addition of EO and PO is optional; and [2] a method of washing an endoscope using an endoscope washer, including the step of washing the endoscope with a mixture including the detergent composition for endoscope washers as described in the above [1], and a protease. The present invention provides a detergent composition for endoscope washers which is less foamed even at a low temperature and is excellent in detergency and storage stability, and a method of washing an endoscope using an endoscope washer in which the above detergent composition is used.

17 Claims, No Drawings

DETERGENT COMPOSITIONS FOR ENDOSCOPE WASHERS

FIELD OF THE INVENTION

The present invention relates to detergent compositions for endoscope washers, and a method of washing an endoscope using an endoscope washer.

BACKGROUND OF THE INVENTION

In recent years, with the progress of advanced medical technology, medical examination and treatment of various regions of a human body such as upper and lower digestive organs, bronchial tubes, abdominal cavity, thoracic cavity, ureteropelvic junction and biliary tract can be made using a medical endoscope without excision. Since various stains such as blood, humor, gastric juice, saliva and cell pieces are adhered to the medical endoscope used for medical examination and treatment, the medical endoscope must be cleaned to surely remove the stains before subjected to subsequent medical examination and treatment in order to prevent infection via the endoscope.

As an apparatus for cleaning the endoscope, there is known an automatic endoscope washer. However, in order to ensure a washing operation of the endoscope washer, it has been always required to previously manually wash the endoscope before using the endoscope washer.

There are conventionally known various detergents for medical instruments such as endoscopes. Also, other detergents such as dishwashing detergents are technically applicable to detergents for endoscopes.

Patent Document 1 discloses an aqueous liquid detergent containing a polyoxyethylene-polyoxypropylene-based low-foaming nonionic surfactant, etc.

Patent Document 2 discloses a detergent composition for automatic dishwashing machines which contains a low-molecular chelate agent, an acrylic acid/maleic acid polymer, an alkaline agent, polypropylene glycol, a reducing sugar, a thickening agent and water.

Patent Document 3 discloses a detergent for automatic dishwashing machines which contains a low-foaming nonionic surfactant, a detergent builder and an aliphatic carboxylic acid having 6 to 10 carbon toms.

Patent Document 4 discloses a detergent composition for containers which contains an alkali metal hydroxide salt, an aliphatic carboxylic acid, a sequestering agent, a surfactant, a high-molecular polymer and water.

Patent Document 5 discloses a detergent composition for medical instruments using a combination of specific nonionic surfactants.

Patent Document 6 discloses a low-foaming alkaline detergent that contains an alkali salt, three kinds of nonionic surfactants containing an ethyleneoxide and propyleneoxide adduct of an aliphatic alcohol, an aliphatic carboxylic acid and water.

Patent Document 7 discloses a detergent for metals which contains a nonionic surfactant such as a polyoxyalkylene alkyl ether, a specific nitrogen-containing organic compound, a carboxylic acid such as an aliphatic carboxylic acid and an alkanol amine compound.

CITATION LIST

Patent Literature

Patent Document 1: JP 2000-96097A
Patent Document 2: JP 2010-163599A
Patent Document 3: JP 6-33100A
Patent Document 4: JP 2006-335896A
Patent Document 5: JP 2009-144070A
Patent Document 6: JP 6-80997A
Patent Document 7: WO 2011/105449A

SUMMARY OF THE INVENTION

Thus, the present invention relates to the following aspects [1] and [2].

[1] A detergent composition for endoscope washers, including a nonionic surfactant (A) represented by the following formula (1), a branched-chain fatty acid having not less than 6 and not more than 10 carbon atoms or a salt thereof (B), a defoaming agent (C) and water,

$$R-O-[(EO)_m/(PO)_n]-H \qquad (1)$$

wherein R represents a branched-chain alkyl group having not less than 7 and not more than 9 carbon atoms; EO represents an ethanediyloxy group; PO represents a propanediyloxy group; m and n each represent an average molar number of addition of the ethanediyloxy or propanediyloxy group in which m is a number of not less than 1 and not more than 30, and n is a number of not less than 2 and not more than 50; and the mark "/" represents that EO and PO may be added either in a random form or in a block form, and an order of addition of EO and PO is optional; and

[2] A method of washing an endoscope using an endoscope washer, including the step of washing the endoscope with a mixture including the detergent composition for endoscope washers as described in the above [1], and a protease.

DETAILED DESCRIPTION OF THE INVENTION

In ordinary cleaning application fields such as dish washing, as the temperature upon washing is raised, the detergency becomes higher. However, since stains attached to an endoscope are composed mainly of proteins such as bloods, a higher washing temperature tends to cause denaturation of the proteins, so that the stains contrarily tend to be hardly removed from the endoscope. For this reason, when washing the endoscope, a washing solution therefor has been used without heating, and water having a very low hardness such as ion-exchanged water and RO water (reverse osmosis membrane-treated water) has been used to enhance a detergency of the washing solution.

However, as the washing temperature is lowered or the hardness of water fed is reduced, foaming is likely to be caused, so that there tends to occur such a concern that a washing performance of the automatic washer is deteriorated.

In addition, upon washing the endoscope, if a strong physical force is applied thereto to enhance a detergency, foaming is likely to occur, so that the physical force such as ultrasonic wave and water flow tends to no longer act on the endoscope, thereby causing such a concern that the detergency tends to be contrarily deteriorated. Also, in the winter season, tap water or ground water tends to be chilled to about 5° C. Under such conditions, even detergents that are free from foaming at a high temperature or substances used as a foam suppressor tend to cause foaming of the washing solution.

On the other hand, the surfactants also tend to be deteriorated in detergency as a foaming property thereof is lowered. When the kinds and concentrations of surfactants are selected so as not to cause foaming even at 5° C., the surfactants exhibit substantially no detergency.

The specific low-foaming nonionic surfactants used in Patent Documents 1 and 2 exhibit a high foam-suppressing effect when used for washing at a high temperature, e.g., used in dishwashers, but contrarily tend to suffer from considerable foaming when used for washing with a low-temperature tap water, in particular, in the winter season.

In Patent Document 3, it is described that low-foaming nonionic surfactants are stabilized with an aliphatic carboxylic acid. However, merely when using an ordinary aliphatic carboxylic acid, the aliphatic carboxylic acid tends to contrarily cause foaming at a low temperature, thereby failing to attain a sufficient foam-suppressing effect.

In the detergent composition described in Patent Document 4, the nonionic surfactants used therein tend to cause remarkable foaming at a low temperature. As a result, the detergent composition tends to be deteriorated in detergency by a physical force such as a water flow, owing to the foams thus produced, so that stains are likely to still remain uncleaned.

In Patent Document 5, it is described that nonionic surfactants are used in combination with fatty acid soaps or the like. However, even when a branched-chain nonionic surfactant is used in combination with an ordinary fatty acid, the resulting composition does not necessarily exhibit a sufficient foam-suppressing effect. In particular, the fatty acids specifically described in Examples of Patent Document 5 tend to cause remarkable foaming at a low temperature.

The low-foaming alkaline detergents described in Patent Document 6 contain three kinds of nonionic surfactants including an ethyleneoxide and propyleneoxide added to an aliphatic alcohol, an aliphatic carboxylic acid such as trimethylhexanoic acid and water. However, the detergents tend to suffer from foaming when used for washing an endoscope at 5° C. using an endoscope washer and therefore tend to be deteriorated in detergency by a physical force such as a water flow, owing to the foams thus produced, so that stains are likely to still remain uncleaned.

The detergents for metals described in Patent Document 7 contains a defoaming agent. However, the detergents tend to fail to exhibit a sufficient foam-suppressing effect when used for washing an endoscope using an endoscope washer. As a result, similarly to the aforementioned detergents, the detergents also tend to be deteriorated in detergency by a physical force such as a water flow, so that stains are likely to still remain uncleaned.

Thus, there are conventionally known no detergents for automatic endoscope washers which hardly suffer from foaming even at a low temperature, and are excellent in detergency.

The present invention aims at providing a detergent composition for endoscope washers which hardly suffer from foaming even at a low temperature (5° C.), and is excellent in detergency and storage stability, and a method of washing an endoscope with the detergent composition using an endoscope washer.

The present invention relates to the following aspects [1] and [2].

[1] A detergent composition for endoscope washers, including a nonionic surfactant (A) represented by the following formula (1), a branched-chain fatty acid having not less than 6 and not more than 10 carbon atoms or a salt thereof (B), a defoaming agent (C) and water,

wherein R represents a branched-chain alkyl group having not less than 7 and not more than 9 carbon atoms; EO represents an ethanediyloxy group; PO represents a propanediyloxy group; m and n each represent an average molar number of addition of the ethanediyloxy or propanediyloxy group in which m is a number of not less than 1 and not more than 30, and n is a number of not less than 2 and not more than 50; and the mark "/" represents that EO and PO may be added either in a random form or in a block form, and an order of addition of EO and PO is optional, and

[2] A method of washing an endoscope using an endoscope washer, including the step of washing the endoscope with a mixture including the detergent composition for endoscope washers as described in the above [1], and a protease.

According to the present invention, there are provided a detergent composition for endoscope washers which hardly suffers from foaming even at a low temperature (5° C.), and is excellent in detergency and storage stability, and a method of effectively washing an endoscope with the detergent composition using an endoscope washer.

In the present invention, the expression "hardly suffer from foaming even at a low temperature (5° C.)" as described herein means that when washing an endoscope using an endoscope washer at a low temperature (5° C.), foaming of a washing solution used therein is suppressed. Also, the expression "from the viewpoint of suppressing foaming at a low temperature" is hereinafter referred to merely as "from the viewpoint of a foam-suppressing property".

Further, the expression "from the viewpoint of enhancing a detergency" is hereinafter referred to merely as "from the viewpoint of a washability".

[Detergent Composition for Endoscope Washers]

The detergent composition for endoscope washers according to the present invention (hereinafter also referred to merely as a "detergent composition") includes a nonionic surfactant (A) represented by the following formula (1) (hereinafter also referred to a "branched-chain nonionic surfactant (A)" or a "component (A)"), a branched-chain fatty acid having not less than 6 and not more than 10 carbon atoms or a salt thereof (B) (hereinafter also referred to a "branched-chain fatty acid (B)" or a "component (B)"), a defoaming agent (C) and water.

wherein R represents a branched-chain alkyl group having not less than 7 and not more than 9 carbon atoms; EO represents an ethanediyloxy group; PO represents a propanediyloxy group; m and n each represent an average molar number of addition of the ethanediyloxy or propanediyloxy group in which m is a number of not less than 1 and not more than 30, and n is a number of not less than 2 and not more than 50; and the mark "/" represents that EO and PO may be added either in a random form or in a block form, and an order of addition of EO and PO is optional.

In the detergent composition according to the present invention, from the viewpoints of a good foam-suppressing property and a good washability, the defoaming agent (C) is preferably a compound represented by the following formula (2), and more preferably further contains a chelate agent (D) and an alkaline agent (E).

wherein $R^1$ represents a hydrogen atom or a hydrocarbon group having not less than 1 and not more than 18 carbon atoms; AO represents an alkanediyloxy group having not less than 3 carbon atoms; p represents an average molar number of addition of the alkanediyloxy group, and is a number of not less than 1 and not more than 500.

In the following, the respective components of the detergent composition according to the present invention are described.

<Nonionic Surfactant (A)>

The detergent composition according to the present invention contains a nonionic surfactant (A) represented by the following formula (1) (branched-chain nonionic surfactant (A)).

$$R\text{—}O\text{-}[(EO)_m/(PO)_n]\text{—}H \quad (1)$$

wherein R represents a branched-chain alkyl group having not less than 7 and not more than 9 carbon atoms; EO represents an ethanediyloxy group; PO represents a propanediyloxy group; m and n each represent an average molar number of addition of the ethanediyloxy or propanediyloxy group in which m is a number of not less than 1 and not more than 30, and n is a number of not less than 2 and not more than 50; and the mark "/" represents that EO and PO may be added either in a random form or in a block form, and an order of addition of EO and PO is optional.

The number of carbon atoms of R in the formula (1) is not less than 7, preferably not less than 8, and not more than 9 from the viewpoint of a good washability and a good foam-suppressing property of the detergent composition. The configuration of the branched chain of the branched-chain alkyl group as R is not particularly limited, and is preferably an isononyl group, a trimethylhexyl group, a 2-ethylhexyl group, an isooctyl group or a dimethylhexyl group from the viewpoint of a good washability and a good foam-suppressing property of the detergent composition.

In the formula (1), the ethanediyloxy group represented by EO is preferably an ethane-1,2-diyloxy group from the viewpoint of a good washability and a good foam-suppressing property of the detergent composition. Also, in the formula (1), the propanediyloxy group represented by PO may be a propane-1,3-diyl group or a propane-1,2-diyl group, and preferably a propane-1,2-diyl group from the viewpoint of a good washability and a good foam-suppressing property of the detergent composition.

In the formula (1), m is not less than 1, preferably not less than 2, more preferably not less than 3, still more preferably not less than 4, further still more preferably not less than 5 and further still more preferably not less than 5.8, and is also not more than 30, preferably not more than 20, more preferably not more than 15, still more preferably not more than 10 and further still more preferably not more than 9, from the viewpoint of a good foam-suppressing property. In the formula (1), n is not less than 2, preferably not less than 3, more preferably not less than 4, still more preferably not less than 4.5 and further still more preferably not less than 4.8, and is also not more than 50, preferably not more than 20, more preferably not more than 10, still more preferably not more than 7, further still more preferably not more than 6 and further still more preferably 5.2, from the viewpoint of a good foam-suppressing property.

In the formula (1), EO and PO are preferably in the form of a random adduct from the viewpoint of a good foam-suppressing property.

The branched-chain nonionic surfactant (A) represented by the formula (1) may be obtained by addition-polymerizing ROH (wherein R is the same as that in the above formula (1)) with ethyleneoxide and propyleneoxide each added in a predetermined amount.

From the viewpoint of a good foam-suppressing property, the nonionic surfactant (A) represented by the formula (1) is preferably at least one compound selected from the group consisting of polyoxyethylene polyoxypropylene isononyl ethers, polyoxyethylene polyoxypropylene 2-ethylhexyl ethers and polyoxyethylene polyoxypropylene dimethylhexyl ethers, and more preferably at least one compound selected from the group consisting of polyoxyethylene polyoxypropylene isononyl ethers.

Many of the endoscope washers are not controlled with respect to a temperature of water used therein upon washing. Therefore, even though there arises no significant foaming problem upon washing with normal temperature water or warm water, when using water having a low temperature (for example, 5° C.), there tends to occur such a concern that foams are hardly eliminated.

On the other hand, in the endoscope washer, water injected under a high pressure is always circulated therethrough in order to enhance a detergency when washing an endoscope using the endoscope washer, so that foaming is more likely to occur therein.

Once the foaming occurs in the endoscope washer, a physical force such as an ultrasonic wave and a water flow is reduced owing to the foams produced and hardly propagated to a surface of the endoscope, which may result in not only deterioration in detergency, but also stopping of the washer owing to erroneous operation of a level sensor for sensing feed or discharge of a washing solution which is mounted in the endoscope washer. The same disadvantage tends to occur when using extremely low-hardness water such as RO water (reverse osmosis membrane-treated water) and ion-exchanged water.

For this reason, it is required to suppress foaming even in the case where low-hardness water (having, for example, a hardness of 1 ppm) is used in the endoscope washer.

Under such a condition that water has a low temperature (e.g., 5° C.) and a low hardness (e.g., a hardness of not less than 0 ppm and not more than 10 ppm), almost all of surfactants exhibit a high foamability, and therefore are unsuitable for the washing operation using the endoscope washer. On the other hand, many of surfactants having a very low foamability are also unsuitable for the washing operation using the endoscope washer because they have an excessively low detergency.

In the detergent composition according to the present invention, when the branched-chain nonionic surfactant (A) is used in a predetermined concentration or more as the surfactant component except for the branched-chain fatty acid (B), it is possible to achieve both of less foaming at a low temperature and a good detergency. Further, if any surfactants other than the branched-chain nonionic surfactant (A) and the branched-chain fatty acid (B) are mixed even in a small amount in the detergent composition, much foaming tends to occur, and the detergent composition tends to be deteriorated in detergency. Therefore, a majority of the surfactants except for the branched-chain fatty acid (B) in the detergent composition are preferably constituted of the branched-chain nonionic surfactant (A).

More specifically, the content of the branched-chain nonionic surfactant (A) in the surfactants except for the branched-chain fatty acid (B) is preferably not less than 90% by mass, more preferably not less than 95% by mass, still more preferably not less than 99% by mass, further still more preferably substantially 100% by mass, and most preferably 100% by mass.

The content of the surfactants other than the branched-chain nonionic surfactant (A) and the branched-chain fatty acid (B) in the whole surfactants contained in the detergent composition is preferably not more than 10% by mass, more preferably not more than 3% by mass and still more preferably substantially 0% by mass, from the viewpoint of a good foam-suppressing property.

The content of the branched-chain nonionic surfactant (A) in the detergent composition according to the present invention is preferably not less than 0.5% by mass, more preferably not less than 1% by mass, still more preferably not less than 2% by mass, further still more preferably not less than 3% by mass, and further still more preferably not less than 4% by mass from the viewpoints of a good washability and a good foam-suppressing property. Also, from the viewpoint of a good storage stability of the detergent composition according to the present invention, the content of the branched-chain nonionic surfactant (A) in the detergent composition is preferably not more than 30% by mass, more preferably not more than 20% by mass, still more preferably not more than 10% by mass, further still more preferably not more than 7% by mass, and further still more preferably not more than 6% by mass.

<Branched-Chain Fatty Acid (B)>

The detergent composition according to the present invention contains a branched-chain fatty acid having not less than 6 and not more than 10 carbon atoms or a salt thereof (B) ("branched-chain fatty acid (B)"). The branched-chain nonionic surfactant (A) usually has a low cloud point that lies in the range of not lower than 10° C. and not higher than 50° C. and therefore tends to be separated from water and become whitely turbid when used under a high temperature condition. However, when using the branched-chain nonionic surfactant (A) in combination with the branched-chain fatty acid (B), the resulting detergent composition according to the present invention can be improved in storage stability without any adverse influence on a low-foaming property and a washability thereof by the branched-chain nonionic surfactant (A).

The number of carbon atoms in a fatty acid of the component (B) is not less than 6, preferably not less than 7 and more preferably not less than 8, and is also not more than 10, preferably not more than 9, and more preferably 9 from the viewpoint of improving a storage stability of the detergent composition according to the present invention without any adverse influence on a low-foaming property and a washability thereof by the branched-chain nonionic surfactant (A).

Specific examples of the branched-chain fatty acid (B) include isodecanoic acids such as methyl nonanoic acid, ethyl octanoic acid, dimethyl octanoic acid, trimethyl heptanoic acid, propyl heptanoic acid, butyl hexanoic acid and diethyl hexanoic acid; isononanoic acids such as methyl octanoic acid, ethyl heptanoic acid, dimethyl heptanoic acid, trimethyl hexanoic acid, propyl hexanoic acid and butyl pentanoic acid; isooctanoic acids such as methyl heptanoic acid, ethyl hexanoic acid and dimethyl hexanoic acid; isoheptanoic acids such as methyl hexanoic acid and ethyl pentanoic acid; isohexanoic acids such as methyl pentanoic acid and ethyl butanoic acid; and salts of these acids. The salts may be in the form of an alkali metal salt such as a sodium salt and a potassium salt, or an alkali earth metal salt such as a calcium salt.

These branched-chain fatty acids (B) may be used alone or in combination of any two or more thereof.

Of these branched-chain fatty acids (B), from the viewpoints of a good storage stability and a good foam-suppressing property of the detergent composition according to the present invention, preferred is at least one compound selected from the group consisting of isononanoic acids, isooctanoic acids and salts of these acids, more preferred is at least one compound selected from the group consisting of isononanoic acids and salts of these acids, and still more preferred is at least one compound selected from the group consisting of 3,5,5-trimethyl hexanoic acid and salts thereof.

The content of the branched-chain fatty acid (B) (in the present invention, the content of the fatty acid salt is calculated in terms of a fatty acid) in the detergent composition according to the present invention is preferably not less than 0.1% by mass, more preferably not less than 1% by mass, still more preferably not less than 2% by mass, further still more preferably not less than 3% by mass, and further still more preferably not less than 4% by mass from the viewpoint of a good storage stability of the detergent composition according to the present invention, and is also preferably not more than 50% by mass, more preferably not more than 20% by mass, still more preferably not more than 15% by mass, further still more preferably not more than 10% by mass, further still more preferably not more than 8% by mass, and further still more preferably not more than 6% by mass from the viewpoints of a good washability and a good foam-suppressing property.

The mass ratio of the content of the branched-chain nonionic surfactant (A) to the content of the branched-chain fatty acid (B) [(A)/(B)] is preferably not less than 1/5, more preferably not less than 1/3, still more preferably not less than 1/2, further still more preferably not less than 3/5 and further still more preferably not less than 4/5, and is also preferably not more than 5/1, more preferably not more than 3/1, still more preferably not more than 2/1 and further still more preferably not more than 6/5, from the viewpoints of a good storage stability and a good foam-suppressing property of the detergent composition according to the present invention.

<Defoaming Agent (C)>

The detergent composition according to the present invention contains a defoaming agent as the component (C). Examples of the defoaming agent include inorganic particles of silica or the like, silicone oils, polyether-modified silicones, alcohols containing a hydrocarbon group having not less than 8 and not more than 24 carbon atoms, and compounds represented by the following formula (2). Of these defoaming agents, from the viewpoints of a good foam-suppressing property and a good storage stability of the detergent composition according to the present invention, preferred are compounds represented by the following formula (2), $$R^1O\text{-}(AO)_p\text{---}H \tag{2}$$

wherein $R^1$ represents a hydrogen atom or a hydrocarbon group having not less than 1 and not more than 18 carbon atoms; AO represents an alkanediyloxy group having not less than 3 carbon atoms; p represents an average molar number of addition of the alkanediyloxy group, and is a number of not less than 1 and not more than 500.

When $R^1$ in the formula (2) is an alkyl group, the number of carbon atoms of $R^1$ is preferably not less than 6, more preferably not less than 8, still more preferably not less than 10 and further still more preferably not less than 12, and is also preferably not more than 18, more preferably not more than 16 and still more preferably not more than 14 from the viewpoints of a good foam-suppressing property and a good storage stability of the detergent composition according to the present invention.

In addition, when $R^1$ is an alkyl group having not less than 1 and not more than 18 carbon atoms, p in the formula (2) is not less than 1, preferably not less than 2, more preferably not less than 3 and still more preferably not less than 4, and is also preferably not more than 30, more preferably not more than 15, still more preferably not more than 10 and further still more preferably not more than 7 from the viewpoints of a good foam-suppressing property and a good storage stability of the detergent composition according to the present invention.

When $R^1$ is a hydrogen atom, p in the formula (2) is preferably not less than 5, more preferably not less than 10 and still more preferably not less than 15, and is also not more than 500, preferably not more than 200, more preferably not more than 100, still more preferably not more than 70, further still more preferably not more than 50 and further still more preferably not more than 30 from the viewpoints of a good foam-suppressing property and a good storage stability of the detergent composition according to the present invention.

The number of carbon atoms in an alkanediyloxy group as AO is preferably not less than 3 and not more than 8, and more preferably not less than 3 and not more than 4, and AO is still more preferably a propanediyloxy group having 3 carbon atoms.

As the defoaming agent, from the viewpoints of a good storage stability and a good foam-suppressing property of the detergent composition according to the present invention, preferred are polypropylene glycol monoalkyl ethers and polypropylene glycols, and more preferred are polypropylene glycol monoalkyl ethers.

These defoaming agents may be used alone or in combination of any two or more thereof.

The average molecular weight of the polypropylene glycols is preferably not less than 300, more preferably not less than 400, still more preferably not less than 500 and further still more preferably not less than 1000, and is also preferably not more than 10000, more preferably not more than 8000, still more preferably not more than 5000 and further still more preferably not more than 2000.

In addition, the average molecular weight of the polypropylene glycol monoalkyl ethers is preferably not less than 100, more preferably not less than 200, still more preferably not less than 300 and further still more preferably not less than 400, and is also preferably not more than 5000, more preferably not more than 3000, still more preferably not more than 1000 and further still more preferably not more than 600.

The content of the defoaming agent (C) in the detergent composition according to the present invention is preferably not less than 0.01% by mass, more preferably not less than 0.02% by mass, still more preferably not less than 0.05% by mass and further still more preferably not less than 0.08% by mass, and is also preferably not more than 2% by mass, more preferably not more than 1% by mass, still more preferably not more than 0.5% by mass, further still more preferably not more than 0.3% by mass and further still more preferably not more than 0.15% by mass, from the viewpoint of a good balance between a foam-suppressing property and a washability of the detergent composition.

The mass ratio of the total content of the branched-chain nonionic surfactant (A) and the branched-chain fatty acid (B) to the content of the defoaming agent (C) [[(A)+(B)]/(C)] is preferably not less than 5, more preferably not less than 10, still more preferably not less than 20, further still more preferably not less than 50, further still more preferably not less than 80 and further still more preferably not less than 90, and is also preferably not more than 500, more preferably not more than 300, still more preferably not more than 200, further still more preferably not more than 150, further still more preferably not more than 130 and further still more preferably not more than 110, from the viewpoints of a good storage stability and a good foam-suppressing property of the detergent composition according to the present invention.

<Water>

The detergent composition according to the present invention contains water. The water used in the detergent composition may be either tap water, ion-exchanged water, RO water or distilled water.

The hardness of the water is preferably not less more than 200 ppm and more preferably not more than 100 ppm from the viewpoint of a good washability.

The water may be mixed with warm water or may be heated to raise a temperature of the detergent composition according to the present invention. The water is preferably used without being heated from the viewpoints of simplifying the construction of a washing device and a economical efficiency. Also, the temperature of the water is preferably not lower than 0° C. and more preferably not lower than 5° C. from the viewpoint of a good washability, and is also preferably not higher than 55° C., more preferably not higher than 35° C. and still more preferably not higher than 25° C. from the viewpoint of low costs.

<Chelate Agent (D)>

The detergent composition according to the present invention preferably contains a chelate agent (sequestering agent) as the component (D). When compounding the chelate agent in the detergent composition, it is possible to efficiently wash off protein stains bonded and adhered to the endoscope by the action of alkali earth metal ions or alkali earth metal salts.

Examples of the chelate agent (D) include aminopolyacetic acids, organic acids, phosphonic acids, phosphoric acids, polycarboxylic acids, and salts of these acids. Specific examples of the chelate agent (D) include aminopolyacetic acids such as nitrilotriacetic acid, iminodiacetic acid, ethylenediaminetetraacetic acid (EDTA), diethylenetriaminepentaacetic acid, glycoletherdiaminetetracetic acid, hydroxyethyliminodiacetic acid, triethylenetetraminehexaacetic acid and djenkolic acid, or salts thereof; organic acids such as diglycolic acid, oxydisuccinic acid, carboxymethyloxysuccinic acid, citric acid, lactic acid, tartaric acid, oxalic acid, malic acid, gluconic acid, carboxymethylsuccinic acid, carboxymethyl tartaric acid and glutamic acid diacetic acid, or salts thereof; phosphonic acids such as aminotri(methylenephosphonic acid), 1-hydroxyethylidene-1,1-diphosphonic acid, ethylenediaminetetra(methylenephosphonic acid) and diethylenetriaminepenta(methylenephosphonic acid), or salts thereof; phosphoric acids such as tripolyphosphoric acid, or salts thereof; and polycarboxylic acids such as polyacrylic acid and polymethacrylic acid, or salts thereof.

These chelate agents may be used alone or in combination of any two or more thereof.

Of these chelate agents (D), from the viewpoint of a good versatility, preferred is at least one compound selected from the group consisting of aminopolyacetic acids and salts thereof, and more preferred is at least one compound selected from the group consisting of ethylenediaminetetraacetic acid (EDTA) and salts thereof.

Examples of the salts of the above acids as the chelate agent (D) include alkali metal salts, quaternary ammonium salts and alkanolamine salts. From the viewpoint of a good corrosion resistance to medical instruments, of these salts, preferred are alkanolamine salts, and more preferred are monoethanolamine salts.

The content of the chelate agent (D) in the detergent composition according to the present invention is preferably not less than 1% by mass, more preferably not less than 2% by mass, still more preferably not less than 3% by mass, further still more preferably not less than 4% by mass and further still more preferably not less than 5% by mass, and is also preferably not more than 50% by mass, more preferably not more than 40% by mass, still more preferably not more than 30% by mass and further still more preferably not more than 25% by mass, from the viewpoints of a good effect of removing protein stains and low costs. The content of the chelate agent (D) is calculated in terms of an acid.

<Alkaline Agent (E)>

The detergent composition according to the present invention preferably contains an alkaline agent as the component (E).

When adding the alkaline agent (E) to the detergent composition according to the present invention, it is possible to further enhance a detergency thereof.

As the alkaline agent (E), there is used at least one compound selected from the group consisting of organic alkali compounds, and hydroxides, carbonates, phosphates and silicates of alkali metals.

Examples of the organic alkali compounds include alkanolamines, alkylamines and quaternary ammonium salts.

Examples of the hydroxides, carbonates, phosphates and silicates of alkali metals include potassium hydroxide, sodium hydroxide, potassium carbonate, sodium carbonate, potassium phosphate, sodium phosphate, a potassium silicate solution No. 1, a sodium silicate solution No. 1, a potassium silicate solution No. 2, a sodium silicate solution No. 2, potassium orthosilicate and potassium orthosilicate.

These alkaline agents may be used alone or in combination of any two or more thereof.

Of these alkaline agents, from the viewpoint of a good corrosion resistance to the endoscope, preferred are alkanolamines, and more preferred are alkanolamines represented by the following formula (3):

$$N(R^2)(R^3)(R^4) \quad (3)$$

wherein $R^2$ is a hydrocarbon group having not less than 1 and not more than 8 carbon atoms which contains not less than 1 and not more than 3 hydroxyl groups; and $R^3$ and $R^4$ are each independently a hydrogen atom, an alkyl group having not less than 1 and not more than 4 carbon atoms, or an alkanol group having not less than 1 and not more than 4 carbon atoms.

In the formula (3), from the viewpoint of a good detergency, $R^2$ is preferably an alkanol group having not less than 2 and not more than 4 carbon atoms, and $R^3$ and $R^4$ are each preferably a hydrogen atom.

Examples of the alkanolamines represented by the above formula (3) include monoethanolamine, monopropanolamine, monoisopropanolamine, diethanolamine, triethanolamine, N-methylpropanolamine, N-dimethyl ethanolamine, 2-amino-2-methyl-1-propanol and trishydroxyaminomethane.

These alkanolamines may be used alone or in combination of any two or more thereof.

Of these alkanolamines represented by the above formula (3), from the viewpoint of a good detergency, preferred is at least one compound selected from the group consisting of monoethanolamine, monopropanolamine, monoisopropanolamine and trishydroxyaminomethane, and more preferred is monoethanolamine.

The content of the alkaline agent (E) in the detergent composition according to the present invention is preferably not less than 1% by mass, more preferably not less than 2% by mass, still more preferably not less than 5% by mass and further still more preferably not less than 10% by mass from the viewpoint of a good detergency, and is also preferably not more than 30% by mass, more preferably not more than 20% by mass and still more preferably not more than 15% by mass from the viewpoint of suppressing damage to a base material of the endoscope.

<pH>

The pH value of the detergent composition according to the present invention as measured at 25° C. is preferably not less than 10.5 and more preferably not less than 11 from the viewpoint of a good washability, and is also preferably not more than 13, more preferably not more than 12.5 and still more preferably not more than 12 from the viewpoint of suppressing damage to a base material of the endoscope.

The detergent composition according to the present invention may be directly used as such, but may be usually used in the form of a washing solution prepared by diluting the detergent composition with water. The dilution ratio of the washing solution from the detergent composition according to the present invention is not particularly limited, and is generally preferably not less than about 50 times by mass and not more than about 1000 times by mass.

In order to attain a high detergency, the pH value of the washing solution upon washing the endoscope is also important. The pH value of a dilute washing solution prepared by diluting the detergent composition according to the present invention 200 times by mass with water as measured at 25° C. is preferably not less than 9.5, more preferably not less than 10 and still more preferably not less than 10.5 from the viewpoint of a good washability, and is also preferably not more than 12 from the viewpoint of suppressing damage to a base material of the endoscope.

<Protease>

The detergent composition according to the present invention may contain a protease. When compounding the protease in the detergent composition, it is possible to efficiently wash off protein stains adhered. Although the protease may be compounded in the detergent composition according to the present invention, a protease-containing detergent composition may be used in combination with the detergent composition according to the present invention. From the viewpoint of a good enzyme stability, it is preferred that the protease-containing detergent composition separately prepared is combined with the detergent composition according to the present invention immediately before used for the washing or upon use.

The protease may be any enzyme belonging to protease (alkaline protease) as long as it has an optimum pH value in the range of from a neutral to an alkaline side. In addition, any two or more proteases capable of satisfying the requirement may also be used in combination with each other.

The alkaline protease that may be used in combination with the detergent composition according to the present invention is preferably subtilisin protease derived from *Bacillus* sp., in particular, subtilisin protease derived from *Bacillus Halodurans* or *Bacillus clausii*. Examples of commercially available products of the alkaline protease include "KAP" available from Kao Corp., "Alcalase", "Savinase", "Everlase", "Esperlase", "Kannase" and "Ovozyme" all available from Novozymes Japan, Inc., and "Purafect" and "Properase" both available from Genencor International Inc. In addition, those proteases described in JP 2007-61101A may also be suitably used.

The detergent composition according to the present invention is preferably used in the form of a dilute washing solution for washing an endoscope. The content (proteolytic activity) of the alkaline protease in the dilute washing solution used in the present invention is preferably not less than 0.01 PU, more preferably not less than 0.05 PU, still more preferably not less than 0.1 PU and further still more preferably not less than 0.5 PU per 1 L of the dilute washing solution, and is also preferably not more than 200 PU, more preferably not more than 100 PU, still more preferably not more than 50 PU and further still more preferably not more than 20 PU per 1 L of the dilute washing solution, from the viewpoints of a good effect of removing protein stains adhered and low costs.

Meanwhile, the proteolytic activity (PU/L) of the dilute washing solution may be measured by the following method.

That is, 1 mL of a 50 mmol/L borate buffer solution (pH: 10.5) containing casein at a concentration of 1 w/v % (Hammerstein grade; available from Merk) is mixed with 0.1 mL of the dilute washing solution to conduct a reaction at 30° C. for 15 min (the resulting reaction solution is hereinafter referred to as a "reaction solution (R)"). Then, 2 mL of a quenching solution (containing 0.11 mol/L of trichloroacetic acid, 0.22 mol/L sodium acetate and 0.33 mol/L of acetic acid) is added to 1.1 mL of the reaction solution (R), and the resulting mixed solution is allowed to stand at room temperature (25° C.) for 10 min. Next, the acid-modified protein is filtered (using a filter paper No. 2 available from Whatman Inc.), and 2.5 mL of an alkaline copper solution [1 w/v % potassium/sodium tartrate aqueous solution: 1 w/v % copper sulfate aqueous solution: sodium hydroxide aqueous solution in which 0.1 mol/L of sodium carbonate is dissolved (concentration of sodium carbonate: 2 w/v %)=1:1:100 (v/v)] is added to the resulting filtrate. A dilute phenol reagent is added to the obtained reaction solution, and after holding the solution under heating for 30 min, the resulting solution is measured for an absorbance thereof at a wavelength of 660 nm (absorbance (S)). Similarly, a blank solution (solution prepared by mixing 2.5 mL of the quenching solution in 1.1 mL of the reaction solution (R) and then adding 0.1 mL of the dilute washing solution to the obtained mixed solution) is measured for an absorbance thereof (absorbance (B)) to calculate an absorbance difference (absorbance (S)—absorbance (B)) from which an amount (P) of an acid-soluble protein degradation product liberated is calculated (an amount of the product in terms of tyrosine is also calculated from a calibration curve separately prepared using tyrosine). The obtained amount (P) of the protein degradation product is divided by the reaction time (15 min) and the amount of the dilute washing solution (0.1 mL) to obtain a proteolytic activity of the washing solution. Meanwhile, in the present invention, "1 PU" means an amount of enzyme capable of liberating the acid-soluble protein as degradation product in an amount corresponding to 1 mmol of tyrosine for 1 min under the above reaction conditions. On the basis of the proteolytic activity obtained by this method, an amount of protease to be compounded in the detergent composition is determined.

The detergent composition according to the present invention may also contain a nonionic surfactant other than the branched-chain nonionic surfactant (A), an anionic surfactant other than the branched-chain fatty acid (B), a cationic surfactant, an amphoteric surfactant, a solvent, a hydrotropic agent, a dispersant, an antioxidant, a pH controller, a thickening agent, a viscosity modifier, a perfume, a colorant, an antiseptic agent, a bleaching agent, a bleaching activator or the like, unless the aimed effects of the present invention are adversely affected. These components may be respectively compounded in a washing solution prepared by diluting the detergent composition.

Examples of the solvent include monovalent alcohols such as ethanol and propanol; and glycol ethers such as ethylene glycol ethyl ether, propylene glycol ethyl ether, ethylene glycol butyl ether and diethylene glycol butyl ether.

Examples of the hydrotropic agent include p-toluenesulfonic acid, benzoic acid, xylenesulfonic acid and salts of these acids, as well as urea, etc.

Examples of the dispersant include polyvinyl pyrrolidone, etc.

Examples of the antioxidant include butylhydroxytoluene, sodium sulfite and sodium hydrogen sulfite.

Examples of the pH controller include citric acid, gluconic acid, malic acid, succinic acid an acetic acid.

[Method of Washing Endoscope Using Endoscope Washer]

The method of washing an endoscope using an endoscope washer according to the present invention is a washing method using a mixture of the detergent composition of the present invention and protease. The protease is the same as described above.

The method of washing an endoscope according to the present invention preferably includes the step of washing the endoscope using a dilute washing solution for endoscopes which is prepared by diluting the detergent composition of the present invention not less than 50 times by mass and not more than 1000 times by mass with water.

Upon washing the endoscope, it is preferred that the endoscope is washed with a flow of the dilute washing solution.

In the method of washing an endoscope according to the present invention, it is preferred that the endoscope washer is provided therein with a liquid section for dipping the endoscope therein, and the flow of the dilute washing solution is fed from above a liquid level in the liquid section. In the endoscope washer having the liquid section, the liquid in the liquid section is preferably circulated therethrough and reused as the dilute washing solution.

As the method of washing an endoscope using an endoscope washer, there are mentioned the method using injected water as described in JP 60-220032A, the method using an ultrasonic wave as described in JP 11-151198A and the like.

In these washing methods, a washing solution stored in a washing tub in which the endoscope can be dipped is injected under a high pressure over a surface of the endoscope or a cover of the washing tub from nozzles disposed above a liquid level therein to wash the endoscope, then discharging of the washing solution, rinsing, and dipping in a disinfectant solution is implemented, thereby rendering the endoscope reusable.

When the nozzles from which the washing solution is injected is disposed above the liquid level, there is such a merit that the injection condition of the washing solution can be visually recognized or the cover of the washing tub can also be washed. On the other hand, there tends to arise such a concern that the washing solution is considerably foamed in the washing tub. If any clogging is caused in washing solution circulating lines and nozzles in the endoscope washer, the detergency thereof tends to be deteriorated, so that the endoscope is washed only to an insufficient extent. As a result, even though the endoscope is subsequently disinfected, germs tend to be still survival so that a concern of nosocomial infection tends to occur. For this reason, it is very important that the injection condition of water from the nozzles can be visually recognized. On the other hand, if foaming of the washing solution is caused in the washing tub, a level sensor fitted in the washing tub tends to be erroneously actuated to stop the washing work, or foams tend to be overflowed from the washing tub, thereby causing a concern of deterioration in detergency, etc.

The detergent composition according to the present invention can be used in the above method of washing the endoscope using the endoscope washer, and when feeding the detergent composition to the endoscope washer, it is possible to wash the endoscope therein without adverse influence of foaming thereof. The viscosity of the detergent composition according to the present invention as measured at 25° C. is preferably not more than 10000 mPa·s, more preferably not more than 1000 mPa·s and still more preferably not more than 300 mPa·s from the viewpoint of facilitated feed of the detergent composition to the automatic endoscope washer. The viscosity of the detergent composition may be measured using a B-type viscometer.

The dilution ratio of the detergent composition according to the present invention when diluted with water is preferably not less than 50 times by mass, more preferably not less than 100 times by mass, and still more preferably not less than 200 times by mass from the viewpoints of a good detergency and low costs, and is also preferably not more than 1000 times by mass, more preferably not more than 500 times by mass and still more preferably not more than 400 times by mass from the viewpoint of a good detergency.

In this case, the washing temperature (temperature of the dilute washing solution) is preferably not lower than 0° C. and more preferably not lower than 5° C., and is also preferably not higher than 55° C., more preferably not higher than 35° C. and still more preferably not higher than 25° C., from the viewpoints of a good washability and low costs. Also, the washing time is preferably not less than 30 s, more preferably not less than 1 min and still more preferably not less than 3 min from the viewpoint of a good washability, and is also preferably not more than 30 min, more preferably not more than 20 min and still more preferably not more than 15 min from the viewpoint of low costs.

The method of washing the endoscope according to the present invention preferably includes a step of feeding the detergent composition of the present invention and a protease preparation into the endoscope washer and diluting the mixture with water to prepare a washing solution. Although the protease may be previously compounded in the detergent composition of the present invention, from the viewpoint of a good enzyme stability, it is preferred that upon washing the endoscope, the separately formulated protease preparation is mixed with the detergent composition of the present invention, and the resulting mixture is diluted with water.

The above respective materials all may be added at the same time, and are preferably added in the order of water, the detergent composition of the present invention and the protease preparation from the viewpoint of suppressing damage to a base material of the endoscope. The protease can exhibit its effects most effectively immediately after addition thereof, and portions where washing with the protease is most needed are portions of a base material of the endoscope to which protein stains are adhered. Therefore, the protease preparation is preferably added after completion of addition of the detergent composition of the present invention. In addition, the protease preparation may be added after the endoscope is washed with the detergent composition of the present invention and water for a while.

With respect to the aforementioned embodiments of the present invention, there are described the following items concerning the detergent composition for endoscope washers and the method of washing an endoscope using an endoscope washer.

<Item 1>
A detergent composition for endoscope washers including a nonionic surfactant (A) represented by the following formula (1), a branched-chain fatty acid having not less than 6 and not more than 10 carbon atoms or a salt thereof (B), a defoaming agent (C) and water,

R—O-[(EO)$_m$/(PO)$_n$]—H (1)

wherein R represents a branched-chain alkyl group having not less than 7 and not more than 9 carbon atoms; EO represents an ethanediyloxy group; PO represents a propanediyloxy group; m and n each represent an average molar number of addition of the ethanediyloxy or propanediyloxy group in which m is a number of not less than 1 and not more than 30, and n is a number of not less than 2 and not more than 50; and the mark "/" represents that EO and PO may be added either in a random form or in a block form, and an order of addition of EO and PO is optional.

<Item 2>
The detergent composition for endoscope washers as described in <Item 1>, wherein R in the formula (1) is preferably a branched-chain alkyl group having not less than 8 and not more then 9 carbon atoms.

<Item 3>
The detergent composition for endoscope washers as described in the <Item 1> or <Item 2>, wherein EO in the formula (1) is preferably an ethane-1,2-diyloxy group.

<Item 4>
The detergent composition for endoscope washers as described in any one of <Item 1> to <Item 3>, wherein PO in the formula (1) is preferably at least one group selected from the group consisting of a propane-1,3-diyloxy group and a propane-1,2-diyloxy group, and more preferably a propane-1,2-diyloxy group.

<Item 5>
The detergent composition for endoscope washers as described in any one of <Item 1> to <Item 4>, wherein m in the formula (1) is preferably not less than 2, more preferably not less than 3, still more preferably not less than 4, further still more preferably not less than 5 and further still more preferably not less than 5.8, and is also preferably not more than 20, more preferably not more than 15, still more preferably not more than 10 and further still more preferably not more than 9.

<Item 6>
The detergent composition for endoscope washers as described in any one of <Item 1> to <Item 5>, wherein n in the formula (1) is preferably not less than 3, more preferably not less than 4, still more preferably not less than 4.5 and further still more preferably not less than 4.8, and is also preferably not more than 20, more preferably not more than 10, still more preferably not more than 7, further still more preferably not more than 6 and further still more preferably not more than 5.2.

<Item 7>
The detergent composition for endoscope washers as described in any one of <Item 1> to <Item 6>, wherein the nonionic surfactant (A) is preferably in the form of a random adduct of EO and PO.

<Item 8>
The detergent composition for endoscope washers as described in any one of <Item 1> to <Item 7>, wherein the nonionic surfactant (A) is contained in an amount of preferably not less than 90% by mass, more preferably not less than 95% by mass, still more preferably not less than 99% by mass, further still more preferably substantially 100% by mass and most preferably 100% by mass on the basis of a total mass of surfactants contained in the detergent composition except for the branched-chain fatty acid having not less than 6 and not more than 10 carbon atoms or the salt thereof (B).

<Item 9>
The detergent composition for endoscope washers as described in any one of <Item 1> to <Item 8>, wherein a content of the nonionic surfactant (A) in the detergent composition is preferably not less than 0.5% by mass, more preferably not less than 1% by mass, still more preferably not less than 2% by mass, further still more preferably not less than 3% by mass and further still more preferably not less than 4% by mass, and is also preferably not more than 30% by mass, more preferably not more than 20% by mass, still more preferably not more than 10% by mass, further still more preferably not more than 7% by mass and further still more preferably not more than 6% by mass.

<Item 10>
The detergent composition for endoscope washers as described in any one of <Item 1> to <Item 9>, wherein the branched-chain fatty acid having not less than 6 and not more than 10 carbon atoms or the salt thereof (B) is preferably at least one compound selected from the group consisting of isodecanoic acids, isononanoic acids, isoheptanoic acids, isohexanoic acids and salts of these acids, more preferably at least one compound selected from the group consisting of isononanoic acids, isooctanoic acids and salts of these acids, still more preferably at least one compound selected from the group consisting of isononanoic acids and salts of these acids, and further still more preferably at least one compound selected from the group consisting of 3,5,5-trimethylhexanoic acid and salts thereof.

<Item 11>
The detergent composition for endoscope washers as described in any one of <Item 1> to <Item 10>, wherein the content of the branched-chain fatty acid having not less than 6 and not more than 10 carbon atoms or the salt thereof (B) in the detergent composition is preferably not less than 0.1% by mass, more preferably not less than 1% by mass, still more preferably not less than 2% by mass, further still more preferably not less than 3% by mass and further still more preferably not less than 4% by mass, and is also preferably not more than 50% by mass, more preferably not more than 20% by mass, still more preferably not more than 15% by mass, further still more preferably not more than 10% by mass, further still more preferably not more than 8% by mass and further still more preferably not more than 6% by mass as calculated in terms of a fatty acid.

<Item 12>
The detergent composition for endoscope washers as described in any one of <Item 1> to <Item 11>, wherein a mass ratio of a content of the branched-chain nonionic surfactant (A) to a content of the branched-chain fatty acid having not less than 6 and not more than 10 carbon atoms or the salt thereof (B) [(A)/(B)] is preferably not less than 1/5, more preferably not less than 1/3, still more preferably not less than 1/2, further still more preferably not less than 3/5 and further still more preferably not less than 4/5, and is also preferably not more than 5/1, more preferably not more than 3/1, still more preferably not more than 2/1 and further still more preferably not more than 6/5.

<Item 13>
The detergent composition for endoscope washers as described in any one of <Item 1> to <Item 12>, wherein the defoaming agent (C) is preferably at least one compound represented by the following formula (2):

$$R^1O\text{-}(AO)_p\text{--}H \qquad (2)$$

wherein $R^1$ represents a hydrogen atom or a hydrocarbon group having not less than 1 and not more than 18 carbon atoms; AO represents an alkanediyloxy group having not less than 3 carbon atoms; p represents an average molar number of addition of AO, and is a number of not less than 1 and not more than 500.

<Item 14>
The detergent composition for endoscope washers as described in <Item 13>, wherein $R^1$ in the formula (2) is an alkyl group, and the number of carbon atoms of $R^1$ is preferably not less than 6, more preferably not less than 8, still more preferably not less than 10 and further still more preferably not less than 12, and is also preferably not more than 18, more preferably not more than 16 and still more preferably not more than 14, and p in the formula (2) is preferably not less than 2, more preferably not less than 3 and still more preferably not less than 4, and is also preferably not more than 30, more preferably not more than 15, still more preferably not more than 10 and further still more preferably not more than 7.

<Item 15>
The detergent composition for endoscope washers as described in <Item 13>, wherein $R^1$ in the formula (2) is a hydrogen atom, and p in the formula (2) is preferably not less than 5, more preferably not less than 10 and still more preferably not less than 15, and is also preferably not more than 200, more preferably not more than 100, still more preferably not more than 70 and further still more preferably not more than 30.

<Item 16>
The detergent composition for endoscope washers as described in any one of <Item 13> to <Item 15>, wherein AO in the formula (2) is preferably an alkanediyloxy group having not less than 3 and not more than 8 carbon atoms, more preferably an alkanediyloxy group having not less than 3 and not more than 4 carbon atoms, still more preferably an alkanediyloxy group having 3 carbon atoms, and further still more preferably a propanediyloxy group.

<Item 17>
The detergent composition for endoscope washers as described in <Item 13>, <Item 15> or <Item 16>, wherein the defoaming agent (C) is polypropylene glycol having an average molecular weight of preferably not less than 300, more preferably not less than 400, still more preferably not less than 500 and further still more preferably not less than 1000, and also preferably not more than 10000, more preferably not more than 8000, still more preferably not more than 5000 and further still more preferably not more than 2000.

<Item 18>
The detergent composition for endoscope washers as described in <Item 13>, <Item 14> or <Item 16>, wherein the defoaming agent (C) is a polypropylene glycol monoalkyl ether having an average molecular weight of preferably not less than 100, more preferably not less than 200, still more preferably not less than 300 and further still more preferably not less than 400, and also preferably not more than 5000, more preferably not more than 3000, still more preferably not more than 1000 and further still more preferably not more than 600.

<Item 19>
The detergent composition for endoscope washers as described in any one of <Item 13> to <Item 18>, wherein a content of the defoaming agent (C) in the detergent composition is preferably not less than 0.01% by mass, more preferably not less than 0.02% by mass, still more preferably not less than 0.05% by mass and further still more preferably not less than 0.08% by mass, and is also preferably not more than 2% by mass, more preferably not more than 1% by mass, still more preferably not more than 0.5% by mass, further still more preferably not more than 0.3% by mass and further still more preferably not more than 0.15% by mass.

<Item 20>
The detergent composition for endoscope washers as described in any one of <Item 13> to <Item 19>, wherein a mass ratio of a total content of the nonionic surfactant (A) and the branched-chain fatty acid having not less than 6 and not more than 10 carbon atoms or the salt thereof (B) to a content of the defoaming agent (C) [[(A)+(B)]/(C)] is preferably not less than 5, more preferably not less than 10, still more preferably not less than 20, further still more preferably not less than 50, further still more preferably not less than 80 and further still more preferably not less than 90, and is also preferably not more than 500, more preferably not more than 300, still more preferably not more than 200, further still more preferably not more than 150, further still more preferably not more than 130 and further still more preferably not more than 110.

<Item 21>
The detergent composition for endoscope washers as described in any one of <Item 1> to <Item 20>, preferably further including a chelate agent (D).

<Item 22>
The detergent composition for endoscope washers as described in <Item 21>, wherein the chelate agent (D) is preferably at least one compound selected from the group consisting of aminopolyacetic acids, organic acids, phosphonic acids, phosphoric acids, polycarboxylic acids, and salts of these acids, more preferably at least one compound selected from the group consisting of aminopolyacetic acids and salts thereof, and still more preferably at least one compound selected from the group consisting of ethylenediaminetetraacetic acid (EDTA) and salts thereof.

<Item 23>
The detergent composition for endoscope washers as described in <Item 21> or <Item 22>, wherein a content of the chelate agent (D) in the detergent composition is preferably not less than 1% by mass, more preferably not less than 2% by mass, still more preferably not less than 3% by mass, further still more preferably not less than 4% by mass and further still more preferably not less than 5% by mass, and is also preferably not more than 50% by mass, more preferably not more than 40% by mass, still more preferably not more than 30% by mass and further still more preferably not more than 25% by mass.

<Item 24>
The detergent composition for endoscope washers as described in any one of <Item 1> to <Item 23>, preferably further including an alkaline agent (E).

<Item 25>
The detergent composition for endoscope washers as described in <Item 24>, wherein the alkaline agent (E) is preferably an alkanolamine, more preferably an alkanolamine represented by the following formula (3), still more preferably at least one alkanolamine selected from the group consisting of monoethanolamine, monopropanolamine, monoisopropanolamine and trishydroxyaminomethane, and further still more preferably monoethanolamine, $$N(R^2)(R^3)(R^4) \quad (3)$$

wherein $R^2$ is a hydrocarbon group having not less than 1 and not more than 8 carbon atoms which contains not less than 1 and not more than 3 hydroxyl groups; and $R^3$ and $R^4$ are each independently a hydrogen atom, an alkyl group having not less than 1 and not more than 4 carbon atoms, or an alkanol group having not less than 1 and not more than 4 carbon atoms.

<Item 26>
The detergent composition for endoscope washers as described in <Item 24> or <Item 25>, wherein a content of the alkaline agent (E) in the detergent composition is preferably not less than 1% by mass, more preferably not less than 2% by mass and still more preferably not less than 5% by mass, and is also preferably not more than 30% by mass, more preferably not more than 20% by mass and still more preferably not more than 15% by mass.

<Item 27>
The detergent composition for endoscope washers as described in any one of <Item 1> to <Item 26>, wherein a pH value of the detergent composition as measured at 25° C. is preferably not less than 10.5 and more preferably not less than 11, and is also preferably not more than 13, more preferably not more than 12.5 and still more preferably not more than 12.

<Item 28>
The detergent composition for endoscope washers as described in any one of <Item 1> to <Item 27>, wherein a pH value of a dilute solution prepared by diluting the detergent composition 200 times by mass with water as measured at 25° C. is preferably not less than 9.5, more preferably not less than 10 and still more preferably not less than 10.5, and is also preferably not more than 12.

<Item 29>
The detergent composition for endoscope washers as described in any one of <Item 1> to <Item 28>, wherein a viscosity of the detergent composition as measured at 25° C. is preferably not more than 10000 mPa·s, more preferably not more than 1000 mPa·s and still more preferably not more than 300 mPa·s.

<Item 30>
A method of washing an endoscope using an endoscope washer, including the step of washing the endoscope with a mixture containing the detergent composition for endoscope washers as described in any one of <Item 1> to <Item 29>, and a protease.

<Item 31>
The method of washing an endoscope using an endoscope washer as described in <Item 30>, wherein a washing solution prepared by diluting the detergent composition for endoscope washers as described in any one of <Item 1> to <Item 29> preferably not less than 50 times by mass, more preferably not less than 100 times by mass and still more preferably not less than 200 times by mass, and also preferably not more than 1000 times by mass, more preferably not more than 500 times by mass and still more preferably not more than 400 times by mass, is used.

<Item 32>
The method of washing an endoscope using an endoscope washer as described in <Item 30> or <Item 31>, wherein the protease is an alkaline protease, and a proteolytic activity of the alkaline protease in the washing solution is preferably not less than 0.01 PU/L, more preferably not less than 0.05 PU/L, still more preferably not less than 0.1 PU/L and further still more preferably not less than 0.5 PU/L, and is also preferably not more than 200 PU/L, more preferably not more than 100 PU/L, still more preferably not more than 50 PU/L and further still more preferably not more than 20 PU/L.

<Item 33>
The method of washing an endoscope using an endoscope washer as described in any one of <Item 30> to <Item 32>, wherein a washing temperature used in the method is not lower than 0° C. and more preferably not lower than 5° C., and is also preferably not higher than 55° C., more preferably not higher than 35° C. and still more preferably not higher than 25° C.

<Item 34>
The method of washing an endoscope using an endoscope washer as described in any one of <Item 30> to <Item 33>, wherein a washing time used in the method is preferably not less than 30 s, more preferably not less than 1 min and still more preferably not less than 3 min, and is also preferably not more than 30 min, more preferably not more than 20 min and still more preferably not more than 15 min.

<Item 35>
A use of the detergent composition for endoscope washers as described in any one of <Item 1> to <Item 29> for a detergent for endoscope washers.

EXAMPLES

Examples 1 to 16 and Comparative Examples 1 to 10

The detergent compositions for endoscope washers as shown in Tables 1 to 3 were prepared, and measured for a pH value thereof and also evaluated for a foam-suppressing property, a washability and a storage stability thereof. The results are shown in Tables 1 to 3.

(0) Measurement of pH

The pH value was measured at a temperature of 25° C. using a pH meter "F-21" available from Horiba Ltd.

(1-1) Evaluation of Foam-Suppressing Property

Using an endoscope washing/disinfecting device "OER-2" available from Olympus Medical Systems Corp., 50 mL of the detergent composition (20° C.) was charged together with 10 L of tap water (hardness: 30 ppm) cooled to 5° C. into a washing tub of the device at the same time. The washing time of the device was set to 10 min, and the device was operated to evaluate a foaming state in the device after 10 min according to the following evaluation criteria.

[Evaluation Criteria]

4: Less foaming was caused, no rise of a level of a washing solution was observed, and no problem concerning operation of the washer occurred.

3: Much foaming was caused, slight raise of a level of a washing solution was observed but no problem concerning operation of the washer occurred.

2: Violent foaming was caused, rise of a level of a washing solution was observed, and when washed for a long period of time (5 min or longer), foams were overflowed in some cases, and further the foaming caused deterioration in washability owing to decrease in water pressure and scattering of ultrasonic wave.

1: Considerable foaming was caused, and the device was no longer usable owing to leakage of a large amount of a washing solution.

The detergent composition having Rank 3 or 4 is acceptable, and usable as a detergent composition for endoscope washers.

(1-2) Evaluation of Amount of Foams

A transparent glass cylindrical container (inner diameter: 60 mm; height: 600 mm) capable of visually observing the condition of contents therein was charged with 500 mL of tap water (hardness: 30 ppm) cooled to 5° C. and further with 2.5 mL of the detergent composition (20° C.) to prepare a washing solution. Using a tubing pump "Masterflex L/S" available from Cole Parmer Instruments Co., Ltd., the washing solution in the cylindrical container was sucked up at a flow rate of 1.5 L/min and fed to a nozzle, and then injected from the nozzle onto a level surface of the washing solution in the cylindrical container in the direction perpendicular to the level surface, thereby circulating the washing solution. The nozzle had an inner diameter of 2 mm, and was disposed such that a tip end thereof was located 25 cm above the level surface of the washing solution in the cylindrical container. The washing solution was injected from the nozzle in the form of a bar-like flow.

The washing solution was circulated for 2 min, and then allowed to stand for 1 min. Thereafter, the amount of foams remaining in the cylindrical container was read out from graduations marked at the intervals of 10 mL on the cylindrical container.

(2) Evaluation of Washability

Model stains containing water, glycerin, serum, mucin, wheat flour and safranin as described in EN/ISO15883-5 Annex R were applied in an amount of 10 mg/cm$^2$ onto a 16 mm-diameter circle region of a test piece (3 cm×8 cm×1 mm in thickness) made of Teflon (registered trademark), and dried at room temperature for 1 h. The thus stained test piece was used for the following experiment.

The stained test piece was fixed in an endoscope washing/disinfecting device "OER-2" available from Olympus Medical Systems Corp., and 10 L of tap water (hardness: 30 ppm) cooled to 5° C. was charged into a washing tub of the device. Immediately after initiation of the washing operation, 50 mL of the detergent composition for endoscope washers and 5 mL of "Savinase" (available from Novozymes Japan, Inc.; protease; enzymatic activity: 12 PU/mL) were directly charged into the washing tub. The concentration of the detergent composition for endoscope washers in the washing solution was 0.5% by mass, and the concentration of "Savinase" in the washing solution was 0.05% by mass. After the elapse of 10 min from the initiation of the washing operation, the operation of the device was stopped to discharge the washing water therefrom. Then, the test piece was taken out from the device and moderately rinsed in a water tank filled with 1000 mL of separately prepared ion-exchanged water at 20° C. After drying, the test piece was observed by naked eyes to examine whether or not any stains remained thereon (pre-CBB dyeing judgment). Thereafter, the test piece on which no remaining stains were observed by naked eyes was dipped in a coomassie protein assay reagent (reagent attached to a protein determination kit available from Thermo Scientific K.K.) for 3 min and subjected to CBB dyeing. The dyed test piece was fully rinsed with ion-exchanged water, and the dyeing condition thereof was observed to examine whether or not a trace amount of stains still remained thereon (post-CBB dyeing judgment). The judgments were carried out according to the following evaluation criteria.

[Evaluation Criteria]

5: In any of the judgments before and after CBB dyeing, no remaining stains were recognized.

4: In the judgment before CBB dyeing, no remaining stains were recognized, but in the judgment after CBB dyeing, remaining protein stains having a size of not more than 0.5 cm$^2$ were partially recognized.

3: In the judgment before CBB dyeing, no remaining stains were recognized, but in the judgment after CBB dyeing, remaining protein stains were recognized on a whole surface of the test piece.

2: Even in the judgment before CBB dyeing, a slight amount of remaining stains were recognized.

1: In the judgment before CBB dyeing, a large amount of remaining blood stains were recognized.

Rank 4 or 5 was acceptable without any practical problem for reuse, i.e., it was recognized that the test piece was well washed.

(3-1) Evaluation 1 of Storage Stability (50° C.)

The detergent composition for endoscope washers was placed in a transparent glass container and stored in a constant-temperature oven at 50° C. for one day. Thereafter, the detergent composition was observed by naked eyes to examine an appearance thereof, and evaluated according to the following evaluation criteria.

[Evaluation Criteria]
 A: Transparent and uniform; and
 B: Separated into two layers, or precipitates were produced.
(3-2) Evaluation 2 of Storage Stability (50° C.)
 The storage stability was evaluated by using the following evaluation criteria in place of those described in the above (3-1).
[Evaluation Criteria]
 A: Transparent and uniform;
 B: Whitely turbid, but returned to a transparent and uniform state when cooled to normal temperature; and
 C: Separated into two layers, or precipitates were produced.

(4) Evaluation of Storage Stability (5° C.)
 The detergent composition for endoscope washers was placed in a transparent glass container and stored in a constant-temperature oven at 5° C. for one day and for one week. Thereafter, the detergent composition was observed by naked eyes to examine an appearance thereof, and evaluated according to the following evaluation criteria.
[Evaluation Criteria]
 A: Transparent and uniform;
 B: Kept in a transparent and uniform state after one day, but slightly separated, or precipitates were produced after one week; and
 C: Separated, or precipitates were produced after one day.

TABLE 1

|  | Examples | | | | | | | |
| --- | --- | --- | --- | --- | --- | --- | --- | --- |
|  | 1 | 2 | 3 | 4 | 5 | 6 | 7 | 8 |
| Detergent composition for endoscope washers (mass %) Component (A) | | | | | | | | |
| Branched-chain nonionic surfactant (1) | 5 | 5 | 5 | 5 | — | 5 | 3 | 7 |
| Branched-chain nonionic surfactant (2) | — | — | — | — | 5 | — | — | — |
| Component (B) | | | | | | | | |
| Trimethylhexanoic acid (branched chain: C9) | 5 | 5 | 5 | — | 5 | 8 | 5 | 5 |
| 2-Ethylhexanoic acid (branched chain: C8) | — | — | — | 5 | — | — | — | — |
| 5-Methylhexanoic acid (branched chain: C7) | — | — | — | — | — | — | — | — |
| Component (C) | | | | | | | | |
| Defoaming agent A: HO—(PO)$_{20}$—H | 0.1 | — | — | 0.1 | 0.1 | 0.1 | 0.1 | 0.1 |
| Defoaming agent B: HO—(PO)$_{64}$—H | — | 0.1 | — | — | — | — | — | — |
| Defoaming agent C: C12—O—(PO)$_5$—H | — | — | 0.1 | — | — | — | — | — |
| Defoaming agent D: C16—O—(PO)$_{10}$—H | — | — | — | — | — | — | — | — |
| Component (D) | | | | | | | | |
| EDTA•4Na | 10 | 10 | 10 | 10 | 10 | 10 | 10 | 10 |
| Component (E) | | | | | | | | |
| MEA | 14 | 14 | 14 | 14 | 14 | 15 | 14 | 14 |
| Ion-exchanged water | | | | Balance | | | | |
| Total (mass %) | 100 | 100 | 100 | 100 | 100 | 100 | 100 | 100 |
| Mass ratio [(A)/(B)] | 1 | 1 | 1 | 1 | 1 | 0.63 | 0.6 | 1.4 |
| pH (25° C.) | 11.1 | 11.1 | 11.1 | 11.1 | 11.1 | 11.0 | 11.1 | 11.1 |
| Evaluation | | | | | | | | |
| (1-1) Foam-suppressing property | 4 | 4 | 4 | 4 | 4 | 3 | 3 | 4 |
| (1-2) Amount of foams (mL) | 80 | 90 | 40 | 70 | 80 | 120 | 110 | 70 |
| (2) Washability | 5 | 5 | 5 | 5 | 5 | 5 | 5 | 5 |
| (3-1) Storage stability (50° C.) | A | A | A | A | A | A | A | A |
| (3-2) Storage stability (50° C.) | A | B | A | B | A | A | A | A |
| (4) Storage stability (5° C.) | A | A | B | A | A | A | A | A |

TABLE 2

|  | Examples | | | | | | | |
| --- | --- | --- | --- | --- | --- | --- | --- | --- |
|  | 9 | 10 | 11 | 12 | 13 | 14 | 15 | 16 |
| Detergent composition for endoscope washers (mass %) Component (A) | | | | | | | | |
| Branched-chain nonionic surfactant (1) | 3 | 5 | 5 | 5 | 5 | 5 | 5 | 7 |
| Branched-chain nonionic surfactant (2) | — | — | — | — | — | — | — | — |
| Component (B) | | | | | | | | |
| Trimethylhexanoic acid (branched chain: C9) | 5 | 5 | 5 | — | 3 | 15 | 5 | 3.5 |
| 2-Ethylhexanoic acid (branched chain: C8) | — | — | — | — | — | — | — | — |
| 5-Methylhexanoic acid (branched chain: C7) | — | — | — | 5 | — | — | — | — |

TABLE 2-continued

|  | Examples | | | | | | | |
|---|---|---|---|---|---|---|---|---|
|  | 9 | 10 | 11 | 12 | 13 | 14 | 15 | 16 |
| Component (C) | | | | | | | | |
| Defoaming agent A: HO—(PO)$_{20}$—H | 0.1 | 0.3 | 0.1 | 0.1 | 0.1 | 0.1 | — | 0.1 |
| Defoaming agent B: HO—(PO)$_{64}$—H | — | — | — | — | — | — | — | — |
| Defoaming agent C: C12—O—(PO)$_5$—H | — | — | — | — | — | — | — | — |
| Defoaming agent D: C16—O—(PO)$_{10}$—H | — | — | — | — | — | — | 0.1 | — |
| Component (D) | | | | | | | | |
| EDTA·4Na | 15 | 10 | 10 | 10 | 10 | 10 | 10 | 10 |
| Component (E) | | | | | | | | |
| MEA | 9 | 14 | 9 | 14 | 14 | 14 | 14 | 14 |
| Ion-exchanged water | Balance | | | | | | | |
| Total (mass %) | 100 | 100 | 100 | 100 | 100 | 100 | 100 | 100 |
| Mass ratio [(A)/(B)] | 0.6 | 1 | 1 | 1 | 1.67 | 0.33 | 1 | 2 |
| pH (25° C.) | 11.6 | 11.1 | 11.0 | 11.1 | 11.1 | 10.9 | 11.1 | 11.1 |
| Evaluation | | | | | | | | |
| (1-1) Foam-suppressing property | 4 | 4 | 4 | 4 | 4 | 3 | 4 | 4 |
| (1-2) Amount of foams (mL) | 90 | 20 | 80 | 60 | 70 | 160 | 80 | 60 |
| (2) Washability | 5 | 4 | 4 | 5 | 5 | 4 | 4 | 5 |
| (3-1) Storage stability (50° C.) | A | A | A | A | A | A | A | A |
| (3-2) Storage stability (50° C.) | A | A | A | B | B | A | B | B |
| (4) Storage stability (5° C.) | A | A | A | A | A | A | B | A |

TABLE 3

|  | Comparative Examples | | | | | | | | | |
|---|---|---|---|---|---|---|---|---|---|---|
|  | 1 | 2 | 3 | 4 | 5 | 6 | 7 | 8 | 9 | 10 |
| Detergent composition for endoscope washers (mass %) | | | | | | | | | | |
| Component (A) | | | | | | | | | | |
| Branched-chain nonionic surfactant (1) | — | — | — | 5 | 5 | 5 | 5 | 5 | 5 | 5 |
| Branched-chain nonionic surfactant (2) | — | — | — | — | — | — | — | — | — | — |
| Component (A') | | | | | | | | | | |
| Straight-chain nonionic surfactant (3) | 5 | — | — | — | — | — | — | — | — | — |
| Straight-chain nonionic surfactant (4) | — | 5 | — | — | — | — | — | — | — | — |
| Straight-chain nonionic surfactant (5) | — | — | 5 | — | — | — | — | — | — | — |
| Component (B) | | | | | | | | | | |
| Trimethylhexanoic acid (branched chain: C9) | 5 | 5 | 5 | — | — | — | — | 5 | — | — |
| 2-Ethylhexanoic acid (branched chain: C8) | — | — | — | — | — | — | — | — | — | — |
| 5-Methylhexanoic acid (branched chain: C7) | — | — | — | — | — | — | — | — | — | — |
| Component (B') | | | | | | | | | | |
| Heptanoic acid (C7) | — | — | — | 5 | — | — | — | — | — | — |
| Octanoic acid (C8) | — | — | — | — | 5 | — | — | — | — | — |
| Nonanoic acid (C9) | — | — | — | — | — | 5 | — | — | — | — |
| Decanoic acid (C10) | — | — | — | — | — | — | 5 | — | — | — |
| 2-Methylbutyric acid (branched-chain: C5) | — | — | — | — | — | — | — | — | 5 | — |
| 2-Hexyldecanoic acid (branched-chain: C16) | — | — | — | — | — | — | — | — | — | 5 |
| Component (C) | | | | | | | | | | |
| Defoaming agent A: HO—(PO)$_{20}$—H | 0.1 | 0.1 | 0.1 | 0.1 | 0.1 | 0.1 | 0.1 | — | 0.1 | 0.1 |
| Defoaming agent B: HO—(PO)$_{64}$—H | — | — | — | — | — | — | — | — | — | — |
| Defoaming agent C: C12—O—(PO)$_5$—H | — | — | — | — | — | — | — | — | — | — |
| Defoaming agent D: C16—O—(PO)$_{10}$—H | — | — | — | — | — | — | — | — | — | — |
| Component (D) | | | | | | | | | | |
| EDTA·4Na | 10 | 10 | 10 | 10 | 10 | 10 | 10 | 10 | 10 | 10 |
| Component (E) | | | | | | | | | | |
| MEA | 14 | 14 | 14 | 15 | 14 | 14 | 14 | 14 | 14 | 14 |
| Ion-exchanged water | Balance | | | | | | | | | |
| Total (mass %) | 100 | 100 | 100 | 100 | 100 | 100 | 100 | 100 | 100 | 100 |
| Mass ratio [(A) or (A')]/[(B) or (B')] | 1 | 1 | 1 | 1 | 1 | 1 | 1 | 1 | 1 | 1 |
| pH (25° C.) | 11.1 | 11.1 | 11.1 | 11.1 | 11.1 | 11.1 | 11.1 | 11.1 | 11.1 | 11.1 |

TABLE 3-continued

| | Comparative Examples | | | | | | | | | |
|---|---|---|---|---|---|---|---|---|---|---|
| | 1 | 2 | 3 | 4 | 5 | 6 | 7 | 8 | 9 | 10 |
| Evaluation | | | | | | | | | | |
| (1-1) Foam-suppressing property | 3 | 2 | 1 | 4 | 2 | 1 | 1 | 2 | 4 | 4 |
| (1-2) Amount of foams (mL) | 180 | 260 | 410 | 70 | 230 | 420 | 530 | 230 | 60 | 80 |
| (2) Washability | 2 | 2 | 3 | 5 | 3 | 3 | 3 | 3 | 4 | 1 |
| (3-1) Storage stability (50° C.) | B | A | A | B | A | B | B | A | B | B |
| (3-2) Storage stability (50° C.) | B | A | A | C | A | C | C | A | C | C |
| (4) Storage stability (5° C.) | A | A | A | B | B | C | C | A | A | C |

As apparently recognized from Tables 1 to 3, the detergent compositions obtained in Examples 1 to 16 were excellent in foam-suppressing property, washability and storage stability as compared to those obtained in Comparative Examples 1 to 10.

The details of the compounds shown in Tables 1 to 3 are as follows.

<Branched-Chain Nonionic Surfactant (A)>
  Branched-chain nonionic surfactant (1): A branched-chain nonionic surfactant "Plurafac LF901" available from BASF Japan, Ltd., as a compound of the formula (1) in which R is a branched-chain alkyl group having 9 carbon atoms; m is 9; n is 5.2; and EO and PO are in the form of a random adduct.
  Branched-chain nonionic surfactant (2): A branched-chain nonionic surfactant "Plurafac LF900" available from BASF Japan, Ltd., as a compound of the formula (1) in which R is a branched-chain alkyl group having 9 carbon atoms; m is 5.8; n is 4.8; and EO and PO are in the form of a random adduct.

<Straight-Chain Nonionic Surfactant (A')>
  Straight-chain nonionic surfactant (3): Assuming that a structure thereof is represented by the formula (1) for the sake of convenience, a compound of the formula (1) in which R is a straight-chain alkyl group having 8 carbon atoms; m is 3.0; n is 2.5; and EO and PO are in the form of a block adduct in which they are added in the order of EO and PO.
  Straight-chain nonionic surfactant (4): Assuming that a structure thereof is represented by the formula (1) for the sake of convenience, a compound of the formula (1) in which R is a straight-chain alkyl group having 8 carbon atoms; m is 7.0; n is 10.0; and EO and PO are in the form of a block adduct in which they are added in the order of EO and PO.
  Straight-chain nonionic surfactant (5): A compound represented by the formula: $R'$—O—$(EO)_{m1}$—$(PO)_{n1}$—$(EO)_{m2}$—H in which R' is a straight-chain alkyl group having 8 carbon atoms; m1 is 3.5; n1 is 2.5; m2 is 3.5; and EO, PO and EO are in the form of a block adduct in which they are added in this order.

<Branched-Chain Fatty Acid (B)>
  Trimethylhexanoic acid: 3,5,5-Trimethylhexanoic acid (branched-chain fatty acid having 9 carbon atoms)
  2-Ethylhexanoic acid (branched-chain fatty acid having 8 carbon atoms)
  5-Methylhexanoic acid (branched-chain fatty acid having 7 carbon atoms)

<Fatty Acid (B') other than (B)>
  Heptanoic acid (straight-chain fatty acid having 7 carbon atoms)
  Octanoic acid (straight-chain fatty acid having 8 carbon atoms)
  Nonanoic acid (straight-chain fatty acid having 9 carbon atoms)
  Decanoic acid (straight-chain fatty acid having 10 carbon atoms)
  2-Methylbutyric acid (branched-chain fatty acid having 5 carbon atoms)
  2-Hexyldecanoic acid (branched-chain fatty acid having 16 carbon atoms)

<Defoaming Agent (C)>
  Defoaming agent A: A compound of the formula (2) in which $R^1$ is a hydrogen atom; AO is a propyleneoxy group; p is 20 on average ("EXCENOL 1020" available from Asahi Glass Co., Ltd.; polyether polyol; molecular weight: 1000).
  Defoaming agent B: A compound of the formula (2) in which $R^1$ is a hydrogen atom; AO is a propyleneoxy group; p is 64 on average ("EXCENOL 3020" available from Asahi Glass Co., Ltd.; polyether polyol; molecular weight: 3200).
  Defoaming agent C: A compound of the formula (2) in which $R^1$ is an alkyl group having 12 carbon atoms; AO is a propyleneoxy group; p is 5 on average.
  Defoaming agent D: A compound of the formula (2) in which $R^1$ is an alkyl group having 16 carbon atoms; AO is a propyleneoxy group; p is 10 on average ("UNILUB MP-60K" available from NOF Corp.).

<Chelate Agent (D)>
  EDTA• 4Na: Tetrasodium ethylenediaminetetraacetate: The respective values appearing in Tables represent an amount in terms of the 4Na salt.

<Alkaline Agent (E)>
  MEA: Monoethanolamine

INDUSTRIAL APPLICABILITY

The detergent composition for endoscope washers according to the present invention is less foamed even at a low temperature and is excellent in detergency and storage stability. The endoscope washer using the detergent composition according to the present invention is capable of effectively washing the endoscope.

The invention claimed is:

1. A detergent composition for endoscope washers, comprising;
   an (A) nonionic surfactant represented by the following formula (1),
   a (B) branched-chain fatty acid having not less than 6 and not more than 10 carbon atoms or a salt thereof,
   a (C) defoaming agent and water, $$R\text{—}O\text{—}[(EO)_m/(PO)_n]\text{—}H \quad (1),$$

wherein R represents a branched-chain alkyl group having not less than 7 and not more than 9 carbon atoms; EO represents an ethanediyloxy group; PO represents a propanediyloxy group; m and n each represent an average molar number of addition of the ethanediyloxy or propanediyloxy group in which m is a number of not less than 1 and not more than 30, and n is a number of not less than 2 and not more than 50; and the mark "/" represents that EO and PO are added in a random form, and an order of addition of EO and PO is optional, wherein a mass ratio of a content of the (A) nonionic surfactant to a content of the (B) branched-chain fatty acid having not less than 6 and not more than 10 carbon atoms or the salt thereof [(A)/(B)] is not less than 1/2 and not more than 2/1, wherein a content of the (A) nonionic surfactant in the detergent composition is not less than 2% by mass and not more than 10% by mass, wherein a content of the (B) branched-chain fatty acid having not less than 6 and not more than 10 carbon atoms or the salt thereof in the detergent composition is not less than 3% by mass and not more than 15% by mass wherein a mass ratio of a total content of the (A) branched-chain non-ionic surfactant and the (B) branched chain fatty acid to a content of the (C) defoaming agent [[(A)+(B)]/(C)] is not less than 50 and not more than 500.

2. The detergent composition for endoscope washers according to claim 1, wherein the (A) nonionic surfactant is contained in an amount of not less than 90% by mass on the basis of a total mass of surfactants contained in the detergent composition except for the (B) branched-chain fatty acid having not less than 6 and not more than 10 carbon atoms or the salt thereof.

3. The detergent composition for endoscope washers according to claim 1, wherein the (C) defoaming agent is at least one compound represented by the following formula (2):

wherein $R^1$ represents a hydrogen atom or a hydrocarbon group having not less than 1 and not more than 18 carbon atoms; AO represents an alkanediyloxy group having not less than 3 carbon atoms; p represents an average molar number of addition of AO, and is a number of not less than 1 and not more than 500.

4. The detergent composition for endoscope washers according to claim 1, wherein a content of the (C) defoaming agent in the detergent composition is not less than 0.05% by mass and not more than 0.5% by mass.

5. The detergent composition for endoscope washers according to claim 1, further comprising a chelate agent (D).

6. The detergent composition for endoscope washers according to claim 1, further comprising an alkaline agent (E).

7. The detergent composition for endoscope washers according to claim 6, wherein the alkaline agent (E) is an alkanolamine.

8. The detergent composition for endoscope washers according to claim 1, wherein the detergent composition has a pH value of not less than 10.5 and not more than 13 as measured at 25° C.

9. A method of washing an endoscope using an endoscope washer, comprising the step of washing the endoscope with a mixture comprising the detergent composition for endoscope washers according to claim 1, and a protease.

10. The method of washing an endoscope using an endoscope washer according to claim 9, wherein the detergent composition for endoscope washers is diluted not less than 50 times by mass and not more than 1000 times by mass upon use.

11. The method of washing an endoscope using an endoscope washer according to claim 9, wherein the protease is an alkaline protease, and a washing solution containing the alkaline protease which has a proteolytic activity of not less than 0.01 PU/L and not more than 200 PU/L is prepared and used for washing the endoscope.

12. The method of washing an endoscope using an endoscope washer according to claim 9, wherein the endoscope is washed at a temperature of not lower than 0° C. and not higher than 55° C.

13. The detergent composition for endoscope washers according to claim 1, wherein m in the formula (1) is not less than 5.8 and not more than 30, and n in the formula (1) is not less than 4.5 and not more than 50.

14. A detergent composition for endoscope washers, comprising an (A) nonionic surfactant represented by the following formula (1), a (B) branched-chain fatty acid having not less than 6 and not more than 10 carbon atoms or a salt thereof, a (C) defoaming agent and water,

wherein R represents a branched-chain alkyl group having not less than 7 and not more than 9 carbon atoms; EO represents an ethanediyloxy group; PO represents a propanediyloxy group; m and n each represent an average molar number of addition of the ethanediyloxy or propanediyloxy group in which m is a number of not less than 5.8 and not more than 30, and n is a number of not less than 4.5 and not more than 50; and the mark "/" represents that EO and PO are added in a random form, and an order of addition of EO and PO is optional, wherein a mass ratio of a total content of the (A) branched-chain non-ionic surfactant and the (B) branched chain fatty acid to a content of the (C) defoaming agent [[(A)+(B)]/(C)] is not less than 50 and not more than 500.

15. The detergent composition for endoscope washers according to claim 14, wherein the detergent composition has a pH value of not less than 10.5 and not more than 13 as measured at 25° C.

16. The detergent composition for endoscope washers according to claim 15, wherein a content of the (C) defoaming agent in the detergent composition is not less than 0.05% by mass and not more than 0.5% by mass.

17. The detergent composition for endoscope washers according to claim 16, further comprising a chelate agent (D) and an alkaline agent (E), wherein the alkaline agent (E) is an alkanolamine.

* * * * *